United States Patent
Liu et al.

(10) Patent No.: US 7,017,386 B2
(45) Date of Patent: Mar. 28, 2006

(54) SELF-TESTING AND SELF-CALIBRATING DETECTOR

(75) Inventors: James Z. Liu, Rockford, IL (US); Andrew Wood, Bloomington, MN (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 11/049,579

(22) Filed: Feb. 2, 2005

(65) Prior Publication Data

US 2006/0042351 A1 Mar. 2, 2006

Related U.S. Application Data

(60) Provisional application No. 60/603,329, filed on Aug. 20, 2004.

(51) Int. Cl.
    *G01N 37/00* (2006.01)
(52) U.S. Cl. .......................................... 73/1.03; 73/1.06
(58) Field of Classification Search .................... None
    See application file for complete search history.

(56) References Cited

U.S. PATENT DOCUMENTS

| 4,474,048 A | * | 10/1984 | Schmidt ...................... 73/1.03 |
| 4,682,502 A | * | 7/1987 | Miyoshi et al. ............... 73/723 |
| 4,793,173 A | * | 12/1988 | Moreth et al. ................ 73/1.03 |
| 4,888,295 A | | 12/1989 | Zaromb et al. ............... 436/161 |
| 5,116,764 A | | 5/1992 | Annino et al. ............... 436/161 |
| 5,329,804 A | * | 7/1994 | Germany et al. ............. 73/1.06 |
| 5,676,820 A | | 10/1997 | Wang et al. .............. 205/777.5 |
| 5,942,103 A | | 8/1999 | Wang et al. ................ 205/787 |
| 5,958,200 A | * | 9/1999 | Kessel ........................ 204/415 |
| 6,321,588 B1 | | 11/2001 | Bowers et al. ............. 73/24.01 |
| 6,519,041 B1 | | 2/2003 | Berthold ..................... 356/477 |
| 6,539,774 B1 | | 4/2003 | Zinck et al. ................. 73/23.2 |
| 6,632,674 B1 | * | 10/2003 | Warburton ..................... 436/8 |
| 6,672,129 B1 | * | 1/2004 | Frederickson et al. ....... 73/1.06 |
| 6,770,391 B1 | | 8/2004 | Nelson et al. ................ 429/22 |
| 2003/0022045 A1 | | 1/2003 | Wells et al. .................. 429/26 |
| 2003/0168337 A1 | | 9/2003 | Mizutani et al. ............ 204/424 |
| 2004/0035179 A1 | * | 2/2004 | Koch .......................... 73/1.05 |
| 2004/0237625 A1 | * | 12/2004 | Rombach et al. ............ 73/1.06 |

FOREIGN PATENT DOCUMENTS

EP          0 469 437      *  5/1992

* cited by examiner

*Primary Examiner*—Robert Raevis
(74) *Attorney, Agent, or Firm*—Kermit D. Lopez; Luis M. Ortiz

(57) ABSTRACT

A self-testing and self-calibrating detector utilizing an internally produced reference gas. A detector that is sensitive to a target analyte as well as a reference gas can be utilized. A gas releasing material, such as a heated metal hydride, releases the reference gas. The partial pressure of the reference gas is known as a temperature dependent physical property of the gas releasing material. During calibration, the material can be heated to release reference gas and a calibration measurement of the gas' partial pressure can be made and compared to an expected value. The comparison can then be utilized to calibrate the detector.

11 Claims, 4 Drawing Sheets

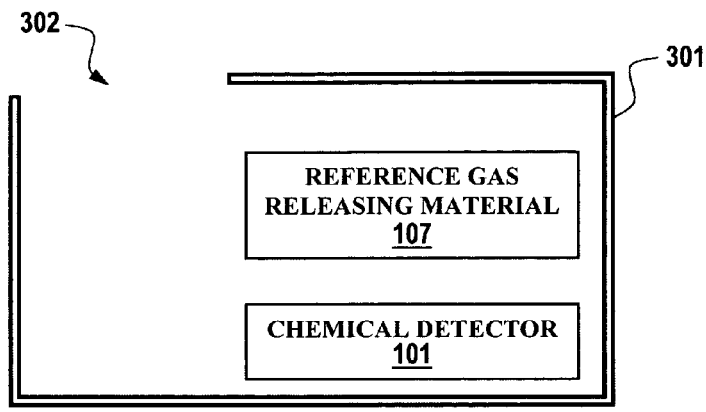
Fig. 3
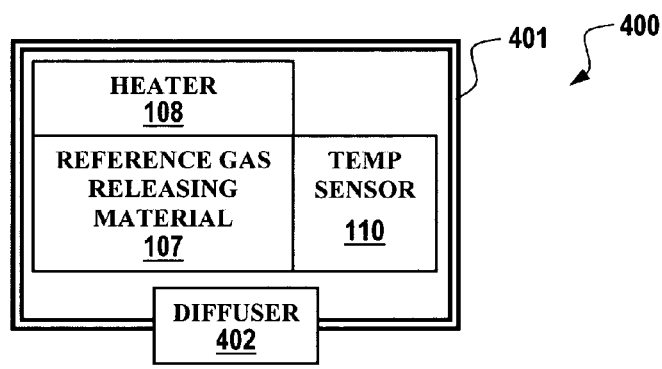
Fig. 4
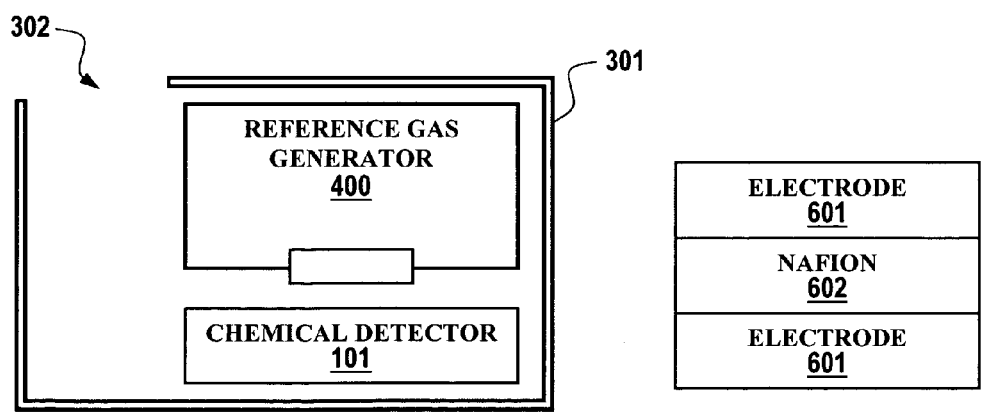
Fig. 5
Fig. 6

SELF-TESTING AND SELF-CALIBRATING DETECTOR

This application claims the benefit of Provisional Application No. 60/603,329, filed Aug. 20, 2004.

TECHNICAL FIELD

Embodiments are related to self-testing and self-calibrating detectors. Embodiments also relate to detectors that test and calibrate themselves by the intermittent internal generation of a reference gas that is used to test and calibrate a detector. Such detectors can be gas detectors, chemical detectors or bio-chemical detectors.

BACKGROUND OF THE INVENTION

Chemical detectors have been in use for some time to sense various gases such as hydrogen, oxygen, carbon monoxide, etc. One form of a chemical detector is an electrochemical cell that uses a catalytic electrode so that the gas to be detected is either oxidized or reduced with the exchange of electrons. The flow of current due to the oxidation or reduction of the gas is then detected as a measure of the concentration of the gas to be detected.

A known problem associated with chemical detectors, however, is referred as "drift," which allows the chemical detectors to lose their sensitivity over time. For example, the working life of an electrochemical cell is determined by the activity of the catalytic electrode that is used to detect chemicals within the detector. This activity is gradually reduced over time by contaminants such that the sensitivity of the detector drifts downward.

Other types of chemical detectors, such as pellistor detectors, biometric detectors, and tin oxide detectors that may be formed as thin film, thick film, sintered or MOSFET devices may have similar problems. If the instrument into which the chemical detector is built is calibrated regularly, adjustment of the chemical detector can compensate for the downward sensitivity drift, and a faulty chemical detector can be replaced immediately.

If the instrument, however, is in a difficult position for servicing, or if calibration of the chemical detector is otherwise not freely available, it is often impossible to confirm that the chemical detector is functioning correctly. Therefore, as the chemical detector reaches the end of its working life, the output of the sensing cell may be low and in chemical alarms may be insufficient to generate an alarm condition. As a result, a situation could arise where toxic levels of chemicals are present, but the chemical detector is incapable of providing the requisite warning.

A substantial effort has been invested in determining a method by which the function of a chemical detector, such as an electrochemical cell, can be checked without the need for an externally generated calibration gas. For example, it has been proposed to use additional electronic components in order to check conductive pathways through the chemical detector. While such methods can uncover broken connections, they do not provide any information on the condition of the electrodes in terms of their ability to react with the chemical to be detected.

External gas sources are often used in industrial settings to calibrate chemical detectors and to correct for drift. Toxic chemical detectors are normally calibrated to measure around the Occupational Exposure Level. For example, for most toxic gases that level, less than 50 ppm, is extremely low. Calibration gas cylinders have a limited shelf life because of the difficulty in preparing a dilute of enough gas/air mixtures, because the materials used to make calibration gas cylinder housings absorb certain toxic gases, and because the mixture can be unstable.

Chemical sensors and biochemical sensors have the same problems as gas sensors and many drift much faster than gas sensors. Electrochemical water content detectors and indirect glucose sensors are examples of the many types of chemical and biochemical sensors. Sensors used for continuous monitoring require dependable periodic testing and calibration. The calibration and testing functions must be easy enough that they are actually used in practice. Self-testing and self-calibration capabilities help make sensor testing and calibration easy.

Oxygen and hydrogen can be generated through the electrolysis of water. The generated oxygen and/or hydrogen can be used for testing and calibrating chemical sensors that rely on the detection of oxygen. The response of the sensor electrodes to hydrogen is similar to that of oxygen, but the electrical current flows in the opposite direction.

The problem with the electrolysis method is that it is difficult to precisely generate a few parts per million (ppm) of gas. Furthermore, some of the gas will dissolve into the water. The amount of gas generated is a function of the voltage, current, temperature, pressure, and other variables. The amount of gas that dissolves into the water is also a function of the voltage, current, temperature, pressure, and other variables. It is difficult to control every variable and therefore it is difficult to generate the gas with the precision required. However, precise generation is necessary for meaningful calibration.

Applications requiring an alarm but not a measurement may not require as accurate a calibration due to loose accuracy requirements and cost considerations, e.g., the UL 2034 regulation for home use CO alarms. Some manufacturers desire a built-in self-testing function for fail-safe purposes. Self-testing and self-calibration are different because self-testing is testing for failures of basic operation, like broken electrodes, while self-calibrating corrects the drift of sensors. Therefore, in self-testing, the amount of gas generated can vary more widely, the heater doesn't have to heat long enough to reach the equilibrium; and the temperature sensor might not be needed. Self-testing can be done more often than self-calibrating because self-testing is easier.

The embodiments discussed herein therefore directly address the shortcomings of the prior art by internally producing a reference gas efficiently, accurately and safely.

BRIEF SUMMARY

The following summary is provided to facilitate an understanding of some of the innovative features unique to the present invention and is not intended to be a full description. A full appreciation of the various aspects of the invention can be gained by taking the entire specification, claims, drawings, and abstract as a whole.

Chemical detectors, including gas detectors and bio-chemical detectors are sensitive to target chemicals and chemical analogues of the target chemical. For example, ozone detectors are also sensitive to chlorine. In this case, chlorine is a chemical analogue of ozone because the ozone detector is cross sensitive to chlorine. A detector can be tested or calibrated using the target chemical, chemical analogues, or a mixture thereof. Sometimes a chemical analog is a gas, such as chlorine or hydrogen. When a chemical detector is tested or calibrated with a gaseous chemical analogue, that gas is called a reference gas.

Table 1 shows cross sensitivities as exemplified by certain chemical detectors. Other detectors will exhibit different cross sensitivities. However, for each chemical detector, known cross sensitivities allow use of a reference gas to calibrate the detector.

TABLE 1

Cross sensitivity effects for certain detectors

| Detector | Reference Gas | Target Chemical Equivalence |
|---|---|---|
| 0 10 ppm acid gas | 10 ppm chlorine | 10 ppm acid gas |
| 0 10 ppm nitrogen dioxide | 10 ppm chlorine | 9 ppm nitrogen dioxide |
| 0 25 ppm hydrogen cyanide | 10 ppm sulphur dioxide | 28 ppm hydrogen cyanide |
| 0 10 ppm chlorine dioxide | 10 ppm chlorine | 4 ppm chlorine dioxide |
| 0 2.5 ppm phosphine | 10 ppm sulphur dioxide | 2 ppm phosphine |
| 0 1 ppm ozone | 2 ppm chlorine | 1 ppm ozone |
| 0 10 ppm hydrogen fluoride | 5 ppm hydrogen chloride | 10 ppm hydrogen fluoride |

A reference gas releasing material releases an amount of reference gas dependent on the temperature of the reference gas releasing material and the partial pressure of the reference gas in the air adjacent to the reference gas releasing material. The partial pressure of a reference gas is the air pressure due only to that particular gas. For example, the air is 79% nitrogen. If the air pressure is 1 atmosphere, then the partial pressure of nitrogen is 0.79 atmospheres.

A reference gas releasing material at a specific temperature releases reference gas until it reaches a specific partial pressure. The specific partial pressure at any given temperature is a physical property of the reference gas generating material that can be measured. If the chemical detector is sensing the amount of a target gas in a gaseous mixture, then the gas released by the reference gas releasing material can be used directly for testing and calibration. If the chemical detector is sensing a target chemical in a liquid mixture, then the reference gas must dissolve into the liquid mixture before it can be used for testing or calibration.

In gaseous mixtures, a gas' partial pressure indicates how much of the gas is present. However, in liquid mixtures partial pressure is not always an accurate way to represent a chemical's presence. As such, the term "partial presence" will be used. In gaseous mixtures "partial pressure" and "partial presence" mean the same thing.

According to one aspect, the self-calibrating chemical detector is a self-calibrating gas detector. It comprises a chemical detector, a measurement circuit, a reference gas generating material, a temperature sensor, a heater, a control circuit, and a calibration circuit. During normal operation, the chemical detector reads a target chemical's partial pressure. The measurement circuit converts the reading into a measurement, and the calibration circuit corrects errors in the measurement. During calibration, a known partial pressure of the reference gas is generated by heating the reference gas generating material, reading the partial pressure with the chemical detector, and comparing the measured partial pressure to the known partial pressure. The calibration circuit is then adjusted to compensate for errors in the measurement.

According to another aspect, the self-testing chemical detector is a self-calibrating gas detector. It comprises a chemical detector, a measurement circuit, a test circuit, an alarm, a control circuit, a heater, and a reference gas releasing material. During all operating modes, the chemical detector reads a target chemical's partial pressure. The measurement circuit converts the reading into a measurement, and test circuit triggers the alarm if the measurement is too high. During testing, a partial pressure of the reference gas high enough to cause an alarm is generated by heating the reference gas generating material.

According to another aspect, the chemical detector and the reference gas releasing material are held inside a unit housing. Reasons are that it is easier and faster to reach and maintain a desired partial pressure in a closed or partially closed volume, that it creates a more easily serviceable unit, and other advantages.

According to yet another aspect, a reference gas generator housing can contain the heater, the temperature sensor, the reference gas releasing material, a diffuser, and possibly, other items. Reasons are that it is easier and faster to reach and maintain a desired partial pressure in a closed or partially closed volume, that it creates a more easily serviceable unit, and other advantages.

According to other aspects, a metal hydride is used as the gas releasing material. Metal hydrides release hydrogen based on the partial pressure of hydrogen and the material's temperature.

According to other aspects, the chemical detector is an electrochemical sensor. Electrochemical sensors exhibit an electrical characteristic, such as an electric current between biased electrodes, based on the presence of certain chemicals.

BRIEF DESCRIPTION OF THE DRAWINGS

The accompanying figures, in which like reference numerals refer to identical or functionally-similar elements throughout the separate views and which are incorporated in and form a part of the specification, further illustrate the embodiments and, together with the detailed description of the invention, serve to explain the principles of the present invention.

FIG. 3 illustrates the use of a unit housing in accordance with an embodiment;

FIG. 4 illustrates the use of a reference gas generator housing in accordance with an embodiment;

FIG. 5 illustrates the use of a unit housing in accordance with an embodiment;

FIG. 6 illustrates one type of electrochemical sensor in accordance with an embodiment;

DETAILED DESCRIPTION OF THE INVENTION

The particular values and configurations discussed in these non-limiting examples can be varied and are cited merely to illustrate embodiments of the present invention and are not intended to limit the scope of the invention.

Figure 1:
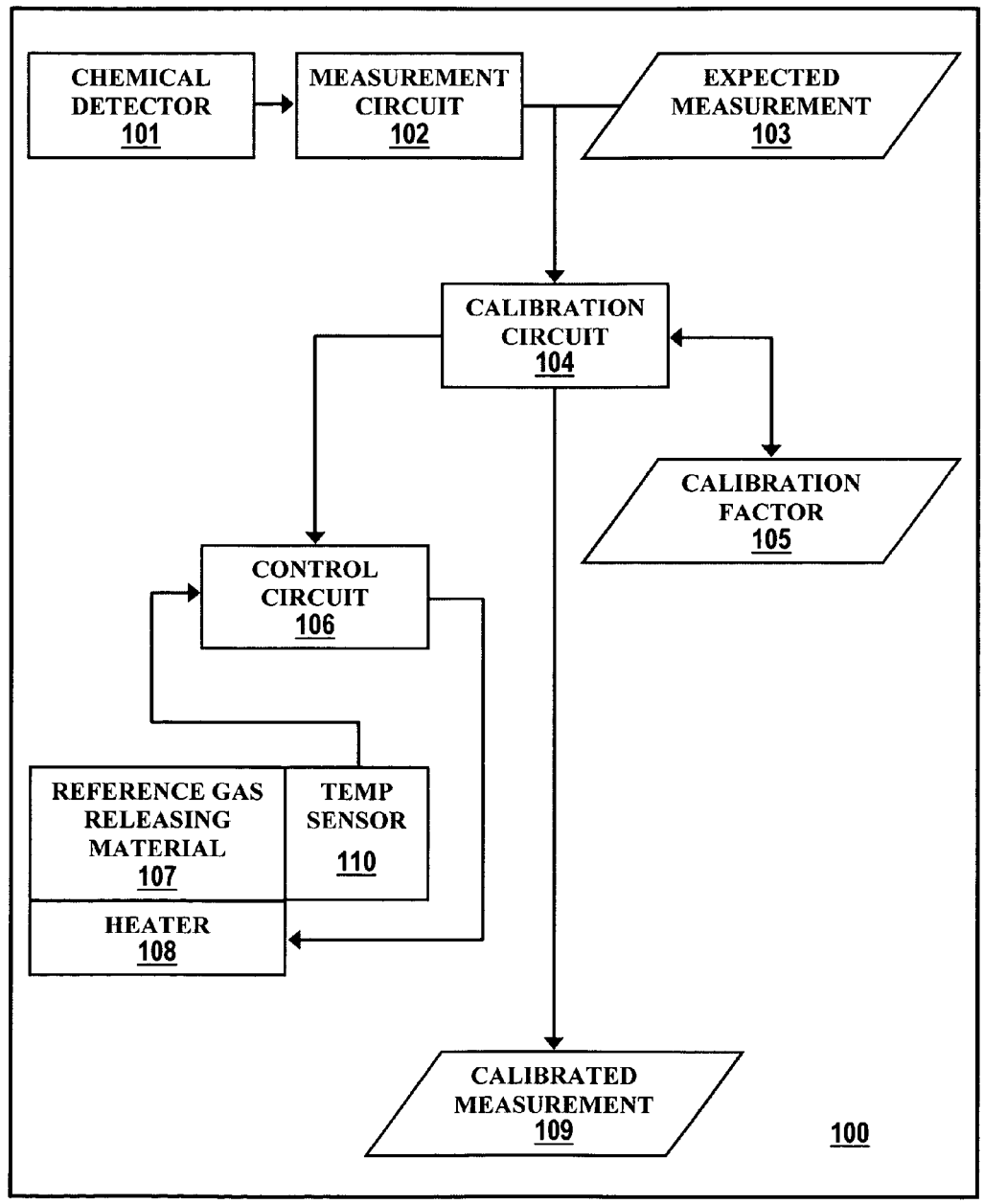
FIG. 1 illustrates a self-calibrating chemical detector according to one embodiment.

FIG. 1 illustrates aspects of a self-calibrating chemical detector 100, which can be implemented in accordance with an embodiment. A chemical detector 101 reads the partial presence of a chemical. As discussed earlier with respect to Table 1, the chemical can be a target chemical, a reference gas, or a combination of the two. A measurement circuit 102 can be utilized to convert the chemical detector 101 readings into a measurement. For example, some chemical detectors exhibit a current between voltage-biased electrodes based on the partial presence of certain chemicals. In this particular embodiment, the measurement circuit 102 can convert the electric current through the chemical detector into a measurement of chemical partial presence.

The measurement can then be passed to the calibration circuit 104. In normal operation, accurate measurements in of chemical partial presence are desired. Therefore, in normal operation the calibration circuit 104 uses the calibration factor 105, a data element, to correct errors in the measurement and produce a calibrated measurement 109, another data element. The self-calibrating chemical detector also has a calibration mode. In calibration mode, the calibration circuit 104 turns on the control circuit 106. The control circuit 106 controls the heater 108.

The heater 108 heats up the reference gas releasing material 107. The temperature sensor 110 reads the temperature of the reference gas releasing material 107 and passes the temperature measurement back to the control circuit 106. The control circuit uses its control of the heater and the temperature measurement to set the temperature of the reference gas releasing material to a known temperature and to hold the temperature steady.

The calibration circuit 104 waits for the partial pressure of the reference gas to rise and stabilize, then acquires a calibration measurement of the reference gas partial presence. A calibration measurement is taken in exactly the same way as a regular measurement is taken in normal operation, but is intended for use in a calibration operation. The calibration circuit also acquires an expected measurement 103. The expected measurement 103, a data element, is what the calibration measurement should be.

The expected measurement 103 is known because the temperature of the reference gas releasing material 107 is known and therefore the reference gas partial pressure is also known because it is a physical property of the reference gas releasing material 107. If the reference gas is being dissolved into a liquid, then the reference gas partial presence is also known. If the reference gas is remaining a gas as part of a gaseous mixture, then the partial presence is the partial pressure. The calibration circuit 104 then calculates the calibration factor 105 by comparing the calibration measurement and the expected measurement 103. The calibration factor 105 is then retained as a data element, completing calibration.

Figure 2:
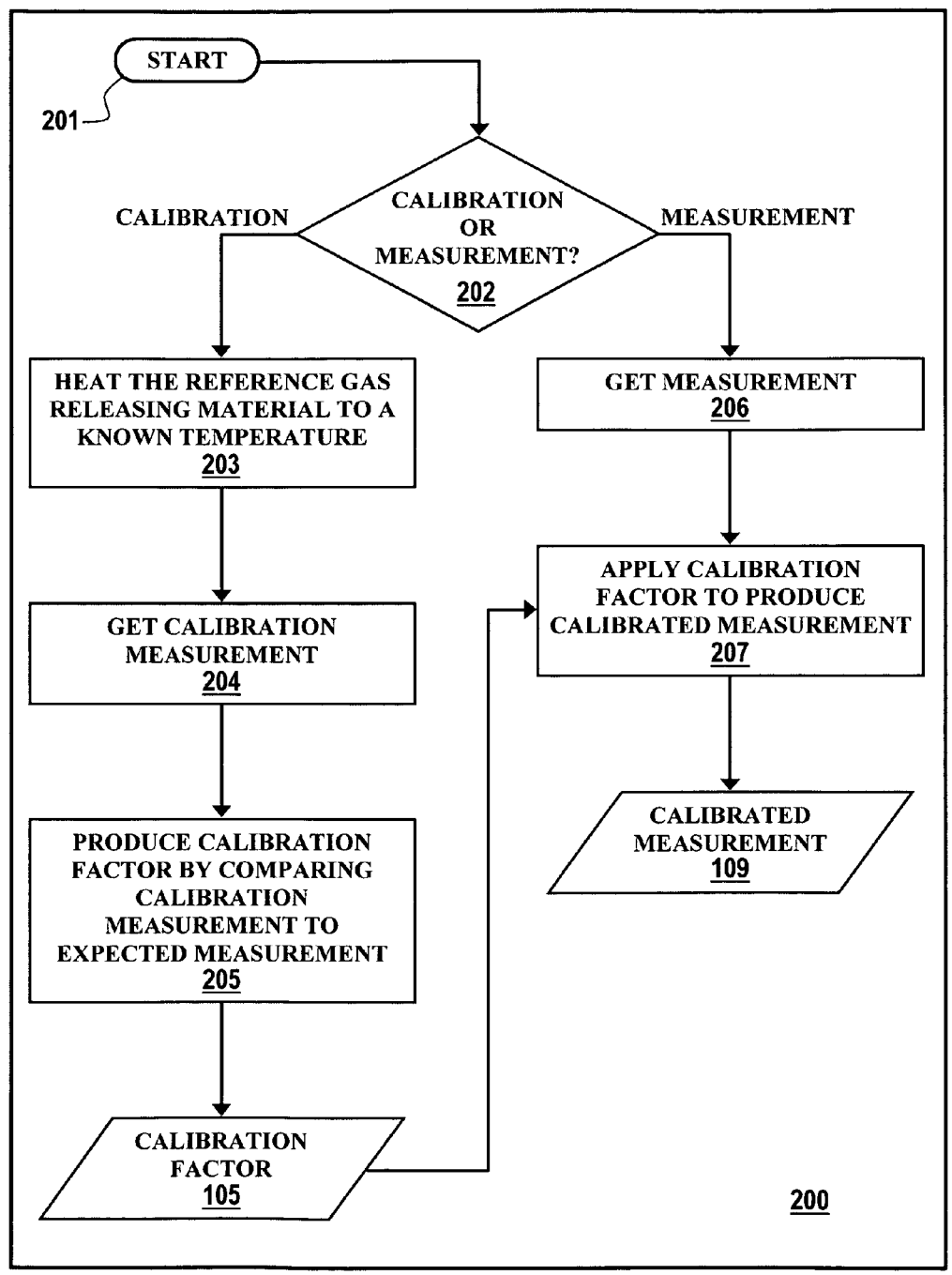
FIG. 2 illustrates a flow chart for operation of a self-calibrating chemical detector according to one or more embodiments.

FIG. 2 illustrates a flow chart clarifying the operation of the embodiment shown in FIG. 1. After the process start 201, the process branches based on the decision 202 of whether to perform a measurement or calibrate the sensor. In measurement mode, a measurement is taken 206, and then adjusted for error 207 to produce a calibrated measurement 109. Error adjustment 207 is performed by applying the calibration factor 105 to the measurement. In calibration mode, the reference gas releasing material is heated to a known temperature 203 and then a calibration measurement is taken 204. The calibration factor 105 is calculated 205 and then retained as a data element.

FIG. 3 illustrates another aspect of the embodiments A unit housing 301 can hold the reference gas releasing material 107 and the gas detector 101. The unit housing 301 creates a single serviceable unit and also helps keep the reference gas from immediately diffusing into the environment during calibration. There is an opening 302 in the unit housing 301 so outside chemicals can reach the chemical detector during normal operation. The unit housing can contain other elements in accordance with other aspects.

FIG. 4 illustrates yet another aspect of the embodiments wherein a reference gas generator 400 comprises a reference gas generator housing 401 that contains the heater 108, reference gas releasing material 107 and temperature sensor 110. A diffuser 402 can control the diffusion of reference gas out of the reference gas generator. The reference gas generator housing can contain other elements in accordance with aspects of other embodiments.

FIG. 5 illustrates another aspect wherein a unit housing 301 contains a reference gas generator 400 and a reference gas detector 101. The unit housing can contain other elements in accordance with aspects of other embodiments.

FIG. 6 illustrates an electrochemical sensor in accordance with another aspect. The sensor comprises 2 electrodes 601 sandwiching a layer of Nafion 602. Nafion 602 is a solid electrolyte that conducts ions. The electrodes 601 are catalytic. A catalyst is something that encourages a chemical reaction, but isn't consumed or produced by the reaction. For example, a carbon monoxide and water reaction can be catalyzed by the electrode to produce carbon dioxide, hydrogen ions, and free electrons. In this example, if the electrodes were DC voltage biased, the hydrogen ions and free electrons could pass through the Nafion 602 creating a measurable electric current.

The sensor depicted in FIG. 6 is known in the art of gas sensing and is illustrated here only as an example of a chemical detector and is not considered a limiting feature of the embodiments disclosed herein. Other chemical detectors that can be used in accordance with other aspects include, but are not limited to, pellistor sensors, a biometric sensors, or tin oxide sensors. Furthermore, other solid electrolytes, such as a high temperature polymer, can be used.

Figure 7:
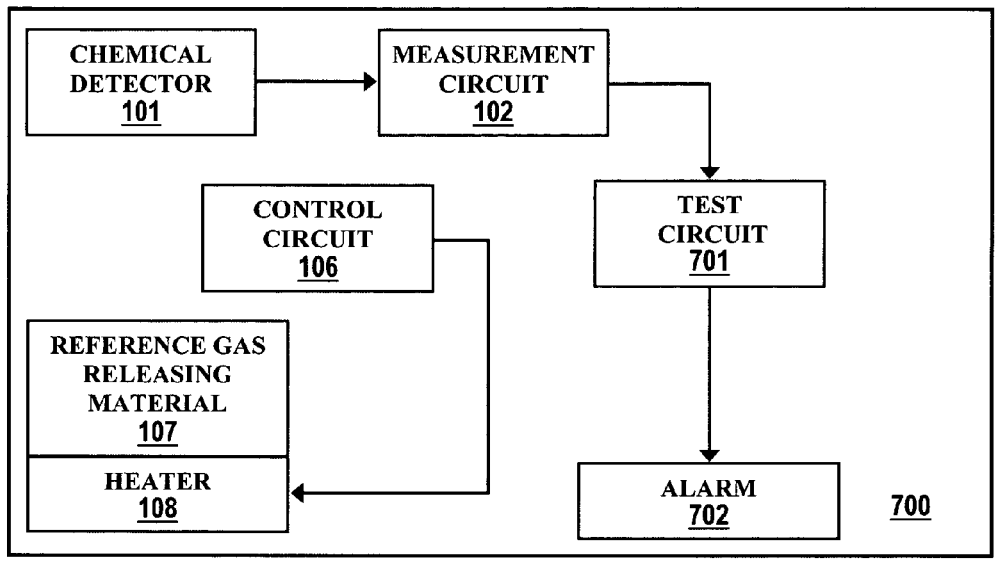
FIG. 7 illustrates a self-testing chemical detector according to another embodiment.

FIG. 7 illustrates aspects of a self-testing chemical detector 700. The self-testing chemical detector 100 has a normal operating mode and a test mode. In all operating modes, the chemical detector 101 reads the partial presence of a chemical. As discussed earlier and shown in Table 1, the chemical can be a target chemical, a reference gas, or a combination of the two.

A measurement circuit 102 can convert the chemical detector 101 reading into a measurement. For example, some chemical detectors exhibit a current between voltage-biased electrodes based on the partial pressures of certain gases. In this case the measurement circuit 102 would convert the electric current through the chemical detector into a measurement of gas partial pressure. The measurement can then be passed to the test circuit 701.

If the test circuit 701 determines that the chemical partial presence is too high then it activates the alarm 702. In test mode, the control circuit 106 turns on the heater 108 that heats up the reference gas releasing material 107 and causes reference gas to be released.

The control circuit 106 and heater 108 are designed to heat the reference gas releasing material 101 to a temperature high enough that the partial presence of the reference gas should be sufficient to be read by the chemical detector 101, measured by the measurement circuit 102, and determined to be too high by the test circuit 701 resulting in the alarm 702 being activated.

Figure 8:
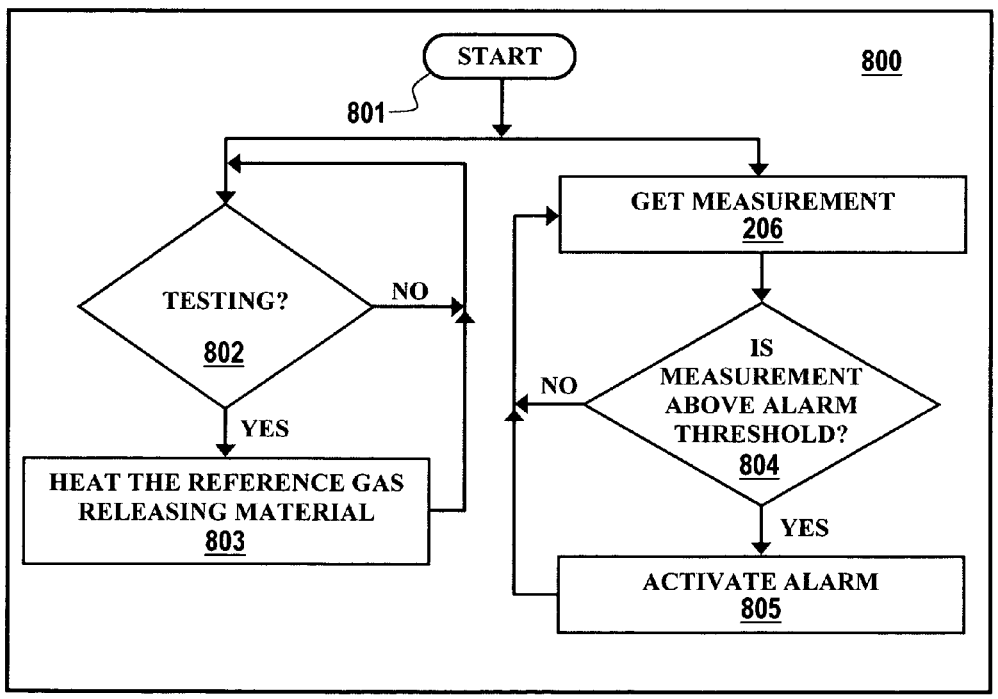
FIG. 8 illustrates a flow chart for operation of a self-testing chemical detector according to one embodiment.

FIG. 8 illustrates a flow chart clarifying the operation of aspects depicted in FIG. 7. After the process start 801, the process branches into a measurement branch and a testing branch. In the measurement branch, a measurement is taken 206, and then compared to an alarm threshold to see if it is too high 804. An alarm threshold an alarm threshold is a value that, if exceeded by a measurement, indicates an alarm should be activated.

The measurement branch continuously measures 206 and compares 804 in an ongoing cycle. If a measurement is too high, then an alarm is activated 804. The testing branch is also repeated in an ongoing cycle. In normal operation mode, nothing is done and the process continuously loops through the testing mode decision box 802. In testing mode, the reference gas releasing material is heated 803 during the cycle.

In accordance with certain embodiments, the reference gas generating material can be a metal hydride. Titanium hydride, magnesium hydride, and magnesium nickel hydride are metal hydrides.

The description as set forth is not intended to be exhaustive or to limit the scope of the invention. Many modifications and variations are possible in light of the above teaching without departing from the scope of the following claims. It is contemplated that the use of the present invention can involve components having different characteristics. It is intended that the scope of the present invention be defined by the claims appended hereto, giving full cognizance to equivalents in all respects.

What is claimed is:

1. A sensor system comprising:
   a chemical detector associated with a measurement circuit that produces a measurement of the partial pressure of a gas from the output of the chemical detector, wherein said chemical detector comprises a electrochemical cell;
   a reference gas releasing material comprising a metal hydride, wherein said reference gas releasing material releases a reference gas such that the partial pressure of the reference gas is a function of the temperature of the reference gas releasing material, wherein a heater is positioned to heat the reference gas releasing material;
   a temperature sensor positioned to measure the temperature of the reference gas releasing material and a control circuit that when activated delivers a known partial pressure of the reference gas to the chemical detector by controlling the heat generated by the heater and thereby the temperature of the reference gas releasing material; and
   a calibration circuit that, during calibration, activates the control circuit, reads a measurement called a calibration measurement from the measurement circuit, and produces a calibration factor by comparing the calibration measurement to an expected measurement, while the calibration circuit also, during regular operation, produces a calibrated measurement from the measurement and the calibration factor.

2. The sensor system of claim 1 further comprising:
   a reference gas generator housing containing the reference gas releasing material, temperature sensor, and the heater; and
   a diffuser in the wall of the reference gas generator housing that controls the diffusion of gases from the inside to the outside of the reference gas generator housing as well as the diffusion of gases from the outside to the inside of the reference gas generator housing.

3. The sensor system of claim 2 wherein the reference gas generator housing comprises a unit housing comprising an opening in the unit housing that permits external chemicals to reach the chemical detector during an operation of the sensor system.

4. The sensor system of claim 1 wherein the measurement circuit converts reading from the chemical detector into a measurement.

5. The sensor system of claim 1 wherein the metal hydride comprises titanium hydride.

6. The sensor system of claim 1 wherein the metal hydride comprises magnesium hydride.

7. The sensor system of claim 1 wherein the metal hydride comprises cell magnesium nickel hydride.

8. A method of producing calibrated gas partial pressure measurements from a chemical detector comprising the steps of:
   intermittently generating a reference gas at a known partial pressure by heating a reference gas releasing material to a known temperature with a heater;
   using a metal hydride as the gas releasing material;
   exposing the chemical detector to the reference gas at a known partial pressure;
   using an electrochemical cell as the chemical detector;
   using the chemical detector to measure the partial pressure of the reference gas during those times that the reference gas is intentionally generated and thereby producing a measurement called a calibration measurement;
   producing a calibration factor by comparing the calibration measurement and an expected measurement;
   producing a calibrated gas partial pressure measurement by applying the calibration factor to a measurement obtained from the chemical detector during those times that the reference gas is not intentionally generated; and
   containing the chemical detector, heater, and reference gas releasing material within a unit housing.

9. The method of claim 8 wherein the metal hydride comprises titanium hydride.

10. The method of claim 8 wherein the metal hydride comprises magnesium hydride.

11. The method of claim 8 wherein the metal hydride comprises magnesium nickel hydride.

* * * * *

UNITED STATES PATENT AND TRADEMARK OFFICE
CERTIFICATE OF CORRECTION

| | | |
|---|---|---|
| PATENT NO. | : 7,017,386 B2 | Page 1 of 1 |
| APPLICATION NO. | : 11/049579 | |
| DATED | : March 28, 2006 | |
| INVENTOR(S) | : James Z. Liu et al. | |

It is certified that error appears in the above-identified patent and that said Letters Patent is hereby corrected as shown below:

Claim 7, column, 8, line 24, delete "cell".

Signed and Sealed this

First Day of August, 2006

JON W. DUDAS
*Director of the United States Patent and Trademark Office*